United States Patent [19]

Gisin et al.

[11] Patent Number: 5,019,515

[45] Date of Patent: May 28, 1991

[54] METHOD OF CONTROLLING AND OPTIMIZING INDUSTRIAL PROCESSES FOR THE MANUFACTURE OF TEXTILE FINISHING AND IMPROVING AGENTS VIA FLOW INJECTION ANALYSIS

[75] Inventors: Markus Gisin, Aesch; Christian Thommen, Basel, both of Switzerland

[73] Assignee: Ciba-Geigy Corporation, Ardsley, N.Y.

[21] Appl. No.: 237,670

[22] Filed: Aug. 23, 1988

Related U.S. Application Data

[63] Continuation of Ser. No. 36,960, Apr. 10, 1987, abandoned.

[30] Foreign Application Priority Data

Apr. 18, 1986 [CH] Switzerland ............... 1568/86
Feb. 3, 1987 [CH] Switzerland ............... 385/87

[51] Int. Cl.$^5$ .................................... G01N 35/08
[52] U.S. Cl. ........................... 436/52; 422/63; 422/81; 436/53; 436/55
[58] Field of Search ............... 436/52, 53, 55; 422/63, 422/81

[56] References Cited

U.S. PATENT DOCUMENTS

| | | | |
|---|---|---|---|
| 3,018,224 | 1/1962 | Ferrari, Jr. ............... | 422/82 |
| 3,435,684 | 4/1969 | Smythe ............... | 436/53 |
| 3,869,067 | 3/1975 | Ashmead et al. ............... | 222/70 |
| 3,933,039 | 1/1976 | Mayer ............... | 73/204 |
| 4,022,575 | 5/1977 | Hansen et al. ............... | 422/81 |
| 4,177,677 | 12/1979 | Ruzicka et al. ............... | 436/52 |
| 4,314,824 | 2/1982 | Hansen et al. ............... | 436/52 |
| 4,315,754 | 2/1982 | Ruzicka et al. ............... | 436/52 |
| 4,362,033 | 12/1982 | Young ............... | 68/207 |
| 4,399,225 | 8/1983 | Hansen et al. ............... | 436/53 |
| 4,440,726 | 4/1984 | Coulson ............... | 436/52 |
| 4,504,443 | 3/1985 | Hansen et al. ............... | 436/52 |
| 4,520,108 | 5/1985 | Yoshida et al. ............... | 436/52 |
| 4,645,647 | 2/1987 | Yoshida et al. ............... | 436/52 |
| 4,680,271 | 7/1987 | Williams ............... | 436/52 |

FOREIGN PATENT DOCUMENTS

| | | | |
|---|---|---|---|
| 749960 | 10/1970 | Belgium ............... | 436/55 |
| 2352735 | 10/1975 | Fed. Rep. of Germany ............... | 436/55 |
| 2273315 | 12/1975 | France . | |
| 67861 | 4/1985 | Japan ............... | 436/52 |

OTHER PUBLICATIONS

Textil Praxis, vol. 22, 581–583, Wevers.
Advances in Instrumentation, vol. 36, 215–221, Piper.
Docherty, A. C., "Automatic Sampling and Analysis of Compound Fertilizers"; Technicon Symposia, vol. 1, pp. 265–271 (1968).

(List continued on next page.)

Primary Examiner—Robert J. Warden
Assistant Examiner—Jill Johnston
Attorney, Agent, or Firm—Kevin T. Mansfield; Edward McC. Roberts

[57] ABSTRACT

A method of on-line controlling and optimizing industrial chemical processes for the manufacture of textile finishing and improving agents to achieve an optimum end point, wherein the improvement comprises the steps of periodic automatic sample taking, over at least the critical state of the process, injecting the samples into a carrier stream, optionally physically and/or chemically manipulating the samples while in the carrier stream, and then transporting the carrier stream to a detector wherein one or more values are measured, said values being used to adjust the process to an optimum end point. The method not only makes possible to determine and monitor the instantaneous state of the process but also, because of the amount of relevant data per unit of time resulting from the method, to drive the process to a desired quality by using the data obtained from the detector for further process control. Each new analysis affords a prognosis on the further reaction course and on the end point of reaction.

12 Claims, 11 Drawing Sheets

OTHER PUBLICATIONS

H. Müller et al., Zeitschrift für Chemie, 24 (1984), pp. 81-93.

J. C. de Andrade et al., Analyst, May 1984, vol. 109, pp. 645-647.

W. E. Van der Linden, Analytica Chimica Acta, 179 (1986) pp. 91-101.

R. A. Mowery, Jr., Intech, May 1984, pp. 51-54.

K. K. Stewart et al., Analytical Chemistry, 54 (1982), pp. 2368-2372.

M. Gisin, paper presented at International Symposium of Flow Injection Analysis, Jun. 1985.

M. Gisin et al., Analytica Chimica Acta, 179 (1986), pp. 149-167.

J. Ruzicka et al., Analytica Chimica Acta, 179 (1986) pp. 1-58.

Ranger, C. B.; "Automated Stream Analysis for Process Control"; vol. 1 (1982) pp. 40-67.

Chemical Analysis, vol. 62 (1981); John Wiley & Sons, Chapters 4, 6 and 7.

FIG. I

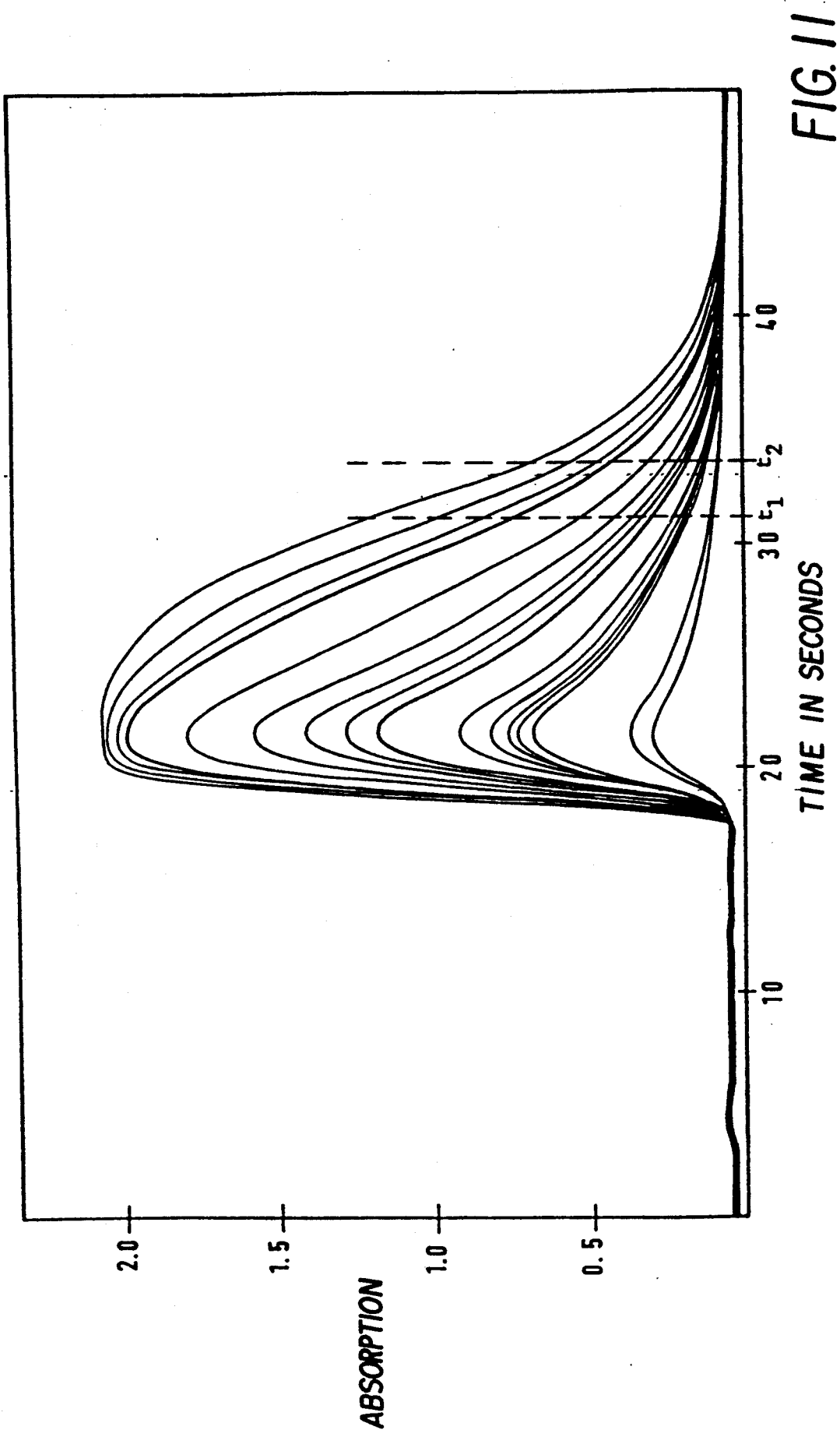

METHOD OF CONTROLLING AND OPTIMIZING INDUSTRIAL PROCESSES FOR THE MANUFACTURE OF TEXTILE FINISHING AND IMPROVING AGENTS VIA FLOW INJECTION ANALYSIS

This application is a continuation of application Ser. No. 036,960, filed 4/10/87 abandoned.

FIELD OF THE INVENTION

The present invention relates to a novel method of controlling and optimising industrial chemical processes by applying the technique of flow injection analysis to processes for the manufacture of textile finishing and improving agents and their intermediates.

BACKGROUND OF THE INVENTION

In recent years, increasing endeavours have been made to automate and optimise processes for the manufacture of textile finishing and improving agents and their intermediates, e.g. dyes and fluorescent whitening agents, both as regards the manufacturing process itself as well as working up. To obtain satisfactory and reproducible results it is necessary to rely on analytical methods which are characterised by the following criteria: short duration of analysis, high frequency of analysis and greater information content per unit of time, as low costs as possible, simplicity, reliability, and minimum space requirements. Equipment that meets these requirements comprises in particular sensors for measuring physical parameters, e.g. temperature, pressure and consumption of starting materials.

These parameters, however, provide no information on the current state and condition of the process (yield of desired product, concentration of by-products, product quality) and the reaction course at any given time. Thus control and maintenance of constant product quality allied to optimum yield is not ensured. Further, it is not possible to make any prognoses from the physical parameters regarding the end point of a reaction, product quality, and yield. Up to now it has been customary to analyse the reaction mass at the end of a process step or at the end of the entire process, thereby ruling out in situ corrections during the reaction course.

Irrespective of the quality of the starting materials, uniform quality of the products of the process together with optimum yield is required at present time of continuous as well as discontinuous processes for the manufacture of textile finishing and improving agents as well as their intermediates.

Discontinuous (i.e. batch) processes in particular often result in products of variable quality induced by the varying quality of the starting materials, and the yield differs from batch to batch.

Accordingly, it is the objective of the present invention to provide an analytical method that meets the aforementioned requirements and to develop a method of controlling and optimising processes for the preparation of textile finishing and improving agents and their intermediates by means of said method, such that control and optimisation can also be carried out preferably on-line.

It has been found that the method of flow injection analysis is preeminently suitable for this purpose.

Flow injection analysis is an automated wet chemical technique based on continuous streams of reagents in capillary tubes, on the injection of reproducible samples into said streams, on the controlled dispersion of the sample zone on its path downstream to the detector, and on precise timing of a single analysis. A flow injection analyzer is characterized by a short start-up time, high injection frequency, and a precise knowledge of the state of the system before and immediately after the individual analysis (modulation).

Flow injection analysis is known per se and reference is made to the following literature: E. H. Hansen and J. Ruzicka "Flow Injection Analysis", John Wiley and Sons, New York, 1981; C. B. Ranger in "Automated Stream Analysis for Process Control", Vol. 1, page 39 et seq., D. P. Manka, Academic Press, 1982.

The primary field of use of flow injection analysis to date has been the automation of methods of wet chemical analysis in the laboratory. Flow injection analysis has also been used for monitoring a small number of continuous chemical processes.

SUMMARY OF THE INVENTION

The present invention relates to a method of controlling and optimising chemical industrial processes, which comprises the use of the method of flow injection analysis for controlling and optimising processes for the preparation of textile finishing and improving agents and their intermediates.

DESCRIPTION OF THE PREFERRED EMBODIMENTS

A preferred embodiment of the method of this invention comprises the use of the method of injection flow analysis for controlling and optimising discontinuous (batch) processes.

The flow injection analyzer which can be employed in the practice of this invention consists e.g. of a reservoir for a carrier solution, e.g. water, a commercially available pump, a conventional sample injection system which injects a reproducible sample volume, e.g. from a by-pass sample taking system, into the stream of the carrier solution, a capillary of suitable length or a stirred mixing chamber for diluting the sample in the carrier stream and for forming a concentration gradient, and a detector, for example a spectrophotometric detector flow cell.

Surprisingly, the method of this invention not only makes it possible to determine and monitor the instant state of the process, e.g. the yield of final product so far obtained and the concentration of by-products, but also, on account of the substantial amount of relevant data per unit of time resulting from the method of flow injection analysis, to drive the process to a desired quality (composition of process products) by using the data obtained from the detector for process control (feedback or, preferably, feed-forward control). Further, each new analysis affords a prognosis on the further reaction course and on the end point of reaction.

The following information to be used for process control is obtained by measuring e.g. spectral data during the reaction:
 the optimum time for terminating the reaction,
 control of yield,
 control of reaction conditions in that deviations from normal are expressed by e.g. increased formation of by-products,
 quality control by determining and identifying by-products.

Textile finishing agents are e.g. dyes and fluorescent whitening agents. Textile improving agents are e.g.

fabric softeners, flame retardants, or dirt, water and oil repellents.

It is most preferred to apply the method of the present invention to processes for the manufacture of dyes and fluorescent whitening agents and their intermediates.

The dyes whose synthesis and processing are monitored and controlled by the method described herein are primarily textile dyes belonging to the widest possible range of chemical classes. These are e.g. anionic dyes such as nitro, aminoketone, ketoneimine, methine, nitrodiphenylamine, quinoline, aminonaphthoquinone or coumarin dyes or also acid dyes based on fustic extract, in particular acid anthraquinone and azo dyes such as monoazo and disazo dyes. Also suitable are basic, i.e. cationic, dyes. These dyes are e.g. the halides, sulfates, methosulfates or metal halide salts, e.g. tetrachlorozincates, of azo dyes such as monoazo, disazo and polyazo dyes, of anthraquinone dyes and phthalocyanine dyes; diphenylmethane and triarylmethane dyes; methine, polymethine and azomethine dyes; of thiazole, ketoneimine, acridine, cyanine, nitro, quinoline, benzimidazole, xanthene, azine, oxazine and thiazine dyes.

Preferred dyes whose synthesis and processing is monitored and controlled by the method described herein are acid dyes of formula

wherein D is the radical of an organic dye of the monoazo or polyazo, metal complex azo, anthraquinone, phthalocyanine, formazan, azomethine, nitroaryl, dioxazine, phenazine or stilbene series, X is a fibre-reactive radical which is attached directly or through a bridge to the radical D, and m is 0, 1, 2, 3, or 4.

Particularly suitable dyes are those listed e.g. in EP-A-0 178 255 on pages 6 or 8, or in EP-A-0 177 449 on pages 13 to 18.

In the present context, the term "dye" shall also be understood as meaning fluorescent whitening agents, e.g. stilbene whiteners, in particular those of the bis-triazinylaminostilbenedisulfonic acid type, of the bis(-styrylbiphenyls) and of the bis(triazolylstilbene)-disulfonic acids.

It will be readily appreciated that, depending on the situation arising from the dye synthesis, precursors and by-products are also encompassed by the process of this invention in addition to dyes and fluorescent whitening agents. The by-products formed during the reaction are especially of great importance, not only with regard to yield, but also as regards shade or the intrinsic colour of the respective dye and/or fluorescent whitening agent.

In principle, the method is susceptible of very broad application and can be used in dye manufacture for monitoring and controlling dye synthesis, for monitoring and controlling educt and product streams, and for quality control.

The technique of flow injection analysis affords the possibility of a near real-time monitoring or direct control of a process, based on the following features of flow injection analysis:

sequential performance of single analyses in the continuous stream of liquid;

short duration of each single analysis, c. 30 seconds, i.e. short response of the analyzer;

high injection frequency, e.g. more than 100 per hour;

good and rapid regeneration of the system, with the baseline indicating the state of the analyzer immediately before and directly after each single analysis.

These features of flow injection analysis define a modulation principle which is of physico-chemical or chemical origin.

The signal recorded by the detector (transient) contains an instrumental contribution, the baseline, and the analytical contribution. In contrast to analyzers which measure directly in the continuous sample stream, the flow injection technique of analysis makes it possible to differentiate unequivocally between the instrumental contribution, i.e. the change in the baseline, and the analytical contribution.

The above features are of great importance for the use of flow injection analysis as part of a computer-controlled process for the manufacture of textile finishing and improving agents and their intermediates.

Flow injection analysis afford various possibilities of providing data on process control.

In addition to the determination of standard parameters important for process control, e.g. concentration of educts, products and by-products, the technique of flow injection analysis is suitable for the selective and reproducible fixing of the end point of the process as well as for making a prognosis on the duration of the further reaction course, and on process quality (educt, product and by-product concentration).

A particularly preferred embodiment of the method of this invention comprises driving a chemical process to a predetermined quality (process end point) by means of flow injection analysis and the data obtained therewith. This process control effected by means of flow injection analysis can be carried out e.g. by simultaneous peak height and peak width measurement of the transients recorded by the detector, e.g. the spectrophotometric detector flow cell. This method of measurement is especially suitable for the control and monitoring of discontinuous processes in the course of which educt and product concentration varies very greatly (e.g. from kilo-mole to mmol range). With this method of measurement it is not necessary to dilute the sample zones. When measuring the peak width, the difference in time between two identical regions of the sample zone (beginning and end of zone) is measured; the identity of such regions of the sample zones refer to the dilution and/or chemical conversion. Substantial differences in concentration can be readily determined during the process by the method of peak width measurement. Peak height measurement is a more sensitive and precise method which is especially suitable for control in the critical range of a process.

Driving a chemical process to a predetermined quality by means of flow injection analysis is effected e.g. by peak height and peak width measurement, with the former being used for the critical range of a process and the latter for the less critical range.

The height of the recorded transient in peak height measurement is proportional to substrate concentration in its lower concentration range. At higher concentrations, the calibration curve becomes increasingly flatter until the system is chemically saturated. It is therefore not possible by means of e.g. filtered samples from a batch process to follow the entire reaction course by means of peak height measurement. By evaluating the peak width it is possible to measure high concentrations with the same system as for end point determinations. The peak width is approximately proportional to the logarithm of analyte concentration. In principle, the peak width can be measured at any height above the baseline. As a consequence of the logarithmic dependance of concentration on peak width, this mode of determination of analyte concentration is less precise than in the case of peak height measurement. The transition from peak width measurement to peak height measurement is made as soon as the analyte concentration reaches the linear range of the peak height measurement of the flow injection system.

Further it is also possible to use a stirred mixing chamber instead of a capillary for forming the concentration gradient. Thus another concentration profile is formed, the calibration curve of the peak width measurement becomes steeper and as a consequence the precision is greater.

Instead of evaluating data recorded by peak width measurement, it is also possible to apply so-called electronic dilution to extend the dynamic range of measurement. Instead of measuring only at the peak maximum, in this mode data, e.g. absorbance values, are measured at different fixed points in time in the descending branch of the gradient. Each of these measuring points covers a limited concentration range of the sample with a linear calibration. The precision of the measurement is best at the peak maximum and deteriorates with increasing distance from the peak maximum. In general, values with lower precision suffice for the control of a production process before the end point is reached.

If a mixing chamber is used instead of a capillary, a greater precision will be obtained on account of the more readily reproducible dilution.

An interesting mode of driving a process to its end point by means of flow injection analysis comprises determining the concentration of a gas in a liquid. The determination is carried out such that the reaction solution containing a gas is passed along a membrane such that the gas diffuses through the membrane into a recipient stream, which is fed into the flow injection analyzer, wherein the gaseous analyte now is recorded after possible reactions to a compound which can be measured by the detector, and the data obtained are used for control. A further procedure comprises feeding a sample of the reaction solution by a valve into a carrier solution and passing this stream along a membrane such that the gas diffuses through said membrane into a second carrier solution containing reagents to form the detectable species. Examples of suitable gases are amines such as methylamine, dimethylamine, $NH_3$, nitrogen oxides, HCl, HCN, $H_2S$, $O_2$, $O_3$ and halogens.

A typical example of the use of this procedure in dye manufacture is the diazotisation of an amine. With respect to the process for the manufacture of one of the most important dye classes, the azo dyes, there still exists a need for simple methods of monitoring an essential synthesis step, viz. the diazotisation reaction. It is possible to monitor diazotisation by determining the nitrogen trioxide concentration. In the course of diazotisation, which is normally carried out with sodium nitrite and hydrochloric acid, nitrogen trioxide forms via the step of nitrous acid and reacts with the amine to form the diazonium compound. During diazotisation, the addition of nitrite or amine will be conveniently monitored via the intensity of the recorded signal, i.e. when the signal has reached a rated value determined by preliminary experimentation, the addition of nitrite or amine is correspondingly corrected. In this manner, overaddition of nitrite or amine can be avoided and the addition of nitrite monitored also during the reaction so that no unwanted secondary reactions occur.

A sensitive analytical method is advantageous for monitoring the diazotisation. The nitrogen trioxide present in the reaction solution diffuses through the membrane into the second carrier stream of the analyzer and reacts with an amine present in the carrier solution to form the diazonium compound to which a coupling component is then added. The carrier solution, which is more or less strongly coloured in accordance with the concentration of the nitrogen trioxide, is analysed in a detector, e.g. a spectrophotometric detector flow cell. When all the amine in the reaction is diazotised, the concentration of nitrogen trioxide increases on further addition of nitrite, resulting in an increase in the intensity of the recorded transient. When the rated value ascertained by calibration is attained, the addition of nitrite is discontinued, i.e. the fluctuations in intensity measured with the spectrophotometer are processed by a process computer which, after making a comparison with the rated value, monitors the reactant streams via a corresponding signal.

The addition of nitrite can also be made in portions, in which case the rate of decrease in concentration is recorded. The end point can be predicted on the basis of these measurements.

Another particularly preferred embodiment of the method of this invention comprises simultaneously determining educt, product and by-product concentration by flow injection analysis. The mixing chamber has proved suitable when the concentrations differ sharply, whereby precise gradient formation over a wide concentration range is made possible and matrix effects (e.g. solvent effects) are eliminated. The elimination of matrix effects is necessary in samples of processes in the course of which, for example, the composition of the solvent is continuously and drastically altered. An exponential gradient is suitable for the dilution, thereby making possible precise measurements over a wide range. The mixing chamber is also suitable for chemical processes in which, at the time the sample is taken and analysed, further reaction of this sample must be quenched e.g. by cooling, for which utility the dilution method is especially suitable, or for chemical processes whose reaction products have differing solubilities in the carrier medium, so that instantaneous dilution prevents these products from precipitating.

The use of a mixing chamber reduces the frequency of analysis; however, what is important for process control is not only the frequency of analysis, but also the amount of information per unit of time or analysis.

In connection with the mixing chamber, an additional method of extending the dynamic range of measurement of flow injection systems can be applied in the process of this invention. This additional method consists of the gradient dilution combined with trapping of a part of the sample zone at variable intervals of time (zone sampling). By integrating this variable dilution step into the analyzer an almost unlimited range of measurement can be converted. When a sample is injected into a stirred mixing chamber, an exponentially decreasing concentration gradient is obtained at the chamber exit. This gradient contains all concentrations between the smallest possible and the greatest possible dilution. By means of a valve it is possible to trap that part of the gradient which corresponds to the desired dilution (zone sampling) and to inject it into a second flow injection system. In this manner, dilutions of up to 1:100,000 can be readily obtained with very good precision (better than 1% relative standard deviation).

At a constant rate of flow, the dilution of the sample depends solely on the time at which the sample is trapped. This enables the dilution of the sample to be controlled on the basis of the actual concentration of the sample by computer control.

The advantages of this technique are that
troublesome substances are diluted, and
the sample can be conditioned in the system.

FIG. 11 is a schematic of the above described method. The constantly changing concentration of the educts and products is illustrated in FIG. 11 by the different gradients. The gradients correspond to the concentration of the sample after leaving the mixing chamber. From each sample which, depending on the immediate state of the process, corresponds to one of the indicated gradients after leaving the mixing chamber, as a segment of the gradient, symbolised by $t_1$ to $t_2$, is injected into a second flow injection system by means of a valve and then analyzed. The time $t_1$ is adjusted to the respective concentration.

Yet another particularly preferred embodiment of the process of this invention comprises controlling a chemical process by reversed flow injection analysis, wherein a sample of the reaction solution is injected into the analyzer at fixed intervals of time, the solution is diluted and, if necessary, pretreated, e.g. by addition of a buffer system, and subsequently one of the active reactants is injected into this dilute sample solution (e.g. a diazonium salt into the solution of a coupling component), and the concentration-dependent signal is recorded in the detector. The data relevant for controlling the process can be evaluated by one of the above mentioned methods.

In principle, the method of this invention is susceptible of very broad application and can be used particularly in the preparation of dyes and fluorescent whitening agents and their precursors and intermediates, for controlling and monitoring the synthesis, for controlling and monitoring educt, product and by-product streams, for analysis and quality control.

Thus, for example, it is possible to control and optimise single phase and multi-phase manufacturing processes. In particular, the method of flow injection analysis is used for on-line control, preferably for the on-line control of a computer-integrated, automated process for the manufacture of textile finishing and improving agents and their intermediates, e.g. dyes, fluorescent whitening agents and their intermediates.

A preferred mode of controlling and optimising chemical industrial processes comprises applying the method of flow injection analysis to the control and optimisation of processes for the preparation of textile finishing and improving agents and their intermediates. The method comprises the following steps by means of computer control (1) sample taking, with or without conditioning of the sample;
(2) injecting the sample into a carrier stream which may or may not contain reagents;
(3) transporting one or more carrier streams by one or more pumps through a capillary of suitable length or by means of a stirred mixing chamber for diluting the sample in said carrier stream and to form a concentration gradient;
(4) transporting the carrier stream to a detector (e.g. a spectrophotometric detector flow cell);
(5) measuring suitable values in the detector;
(6) transmitting the measured values to the computer;
(7) comparing the measured values with a rated value; and
(8) exerting a computer-controlled influence on the process (e.g. modulating the reactant streams).

A salient feature of the process of this invention for controlling and optimising textile finishing and improving agents and their intermediates, in particular dyes and fluorescent whiteners and their intermediates, is the sample taking system, for it is preferably dispersions (slurries) that have to be conditioned before they are fed into the flow injection system. This conditioning can consist of a dissolving and dilution step, so that only dissolved portions are fed into the analyzer. In the process of this invention it is preferrable to use a by-pass sample taking system with continuous filtration;
homogenisation and/or dilution of the sample with a solvent; or
a membrane, e.g. a teflon membrane through which portions of the relevant analyte(s) can diffuse for subsequent monitoring.

By appropriate choice of the sample taking system, substances which interfere with the analysis may be separated.

The process of this invention for controlling and optimising textile finishing and improving agents and their intermediates, in particular dyes and fluorescent whitening agents and their intermediates, preferably comprises applying the method of flow injection analysis to said control and optimisation; the samples required for control and optimisation are pretreated via a by-pass sample taking system with continuous filtration or with a homogenisation or dilution of the sample with a solvent to pretreat or dissolve undissolved constituents, or with a membrane, so that only dissolved portions are fed into the flow injection system and, for covering a wide concentration range, as is necessary for the batchwise production of textile finishing and improving agents and their intermediates, data based on peak height measurement, peak width measurement or electronic dilution or gradient dilution with variable zone sampling, are recorded and processed by the system.

Further salient features of the process of this invention relate to the injection system for which rotary valves have proved especially suitable, as they ensure high precision, as well as pumps for transporting the solutions, particularly suitable pumps being e.g. injection pumps such as piston burettes, as they operate pulse-free, ensure a constant rate of flow, and are exactly controllable and are also able to pump organic and aggressive reagents.

Special advantages of the flow injection analysis technique are the unproblematic use of e.g. unstable detector reagents such as diazonium ions, the self-cleansing nature of the system, and the high measuring frequency which makes feed-forward control possible.

A preferred embodiment of the method of the invention comprises applying the method of flow injection analysis to the control and optimisation of processes for the preparation of textile finishing and improving agents and their intermediates, especially dyes and fluorescent whitening agents and their intermediates, the analyzer comprising:

a sample taking system,
an injection system, one or more carrier streams which may or may not contain reagents, one or more injections pumps for transporting the streams, one or more capillaries or a stirred mixing chamber, and a detector, said sample taking system consisting preferably of a valve for completely dissolved samples, or a valve connected to a continuous filtration, homogenisation and-/or dilution of sample with a solvent or a membrane, whereby only portions of the sample relevant for the analysis or only dissolved amounts of the sample are fed into the analyzer system.

The pumping system consists preferably of an injection pump, e.g. a piston burette.

Advantages of the flow injection analysis technique for on-line control, in contrast to probes in a by-pass line or in a reaction vessel are the separation of analytical signal and baseline as well as the simple possibility of subsequent calibration during the course of the process. By control of the baseline it is possible e.g. to detect a contamination of the flow injection system early and, for example, to take appropriate countermeasures immediately, e.g. by switching on a rinsing cycle, without affecting the monitored process and its control.

Preferred methods are:

Use of a stirred mixing chamber to form the concentration gradient in the flow injection analyzer.

Use of the method of flow injection analysis for controlling and optimising acylation reactions. By acylation is meant the condensation of a fibre-reactive or fibre-unreactive acyl radical with an amine, a hydroxyl group or a thiol group.

Use of the method of flow injection analysis for controlling and optimising diazotisation reactions.

Use of a gas diffusion cell as sample taking or sample pretreatment system for controlling and optimising diazotisation reactions.

Use of the method of flow injection analysis for controlling and optimising coupling reactions.

Use of a sample which has been pretreated by continuous filtration, homogenisation or dilution with a solvent or with a membrane in the flow injection analyzer.

BRIEF DESCRIPTION OF THE FIGURES

FIG. 11 is a schematic of the technique of gradient dilution combined with zone sampling, the constantly changing concentration being illustrated by different gradients and $t_1$ to $t_2$ enclosing a segment of the gradient which is fed from a valve into a second flow injection analysis system.

The invention is illustrated by the following Examples, in which parts and percentages are by weight. The relationship between parts by weight and parts by volume is the same as that between the gram and the cubic centimeter.

EXAMPLE 1

Preparation of 1-amino-3-(2',3'-dibromopropionylamino)-benzene-6-sulfonic acid to exemplify process control by flow injection analysis by measuring and evaluating the height and width of a spectrophotometrically recorded signal, Process: 1-amino-3-(2',3'-dibromopropionylamino)-benzene-6-sulfonic acid is prepared from 1,3-phenylenediamine-4-sulfonic acid by acylation with 2,3-dibromopropionyl chloride. The reaction product is a colourless intermediate which is used, without further processing or purification, as starting material for subsequent process steps in a batch process. It is therefore necessary to find the optimum time for discontinuing the reaction, as too high a concentration of starting material as well as to high a concentration of by-product (diacylated phenylenediamine) will result in quality problems.

Flow injection analyzer: reproducible quality of the above process product is ensured by on-line process control. An azo coupling reaction is carried out as analytical method in the analyzer. The analyzer corresponds to the assembly illustrated in FIG. 1, in which R1 is a reservoir containing aqueous sodium nitrite solution (0.002 mole/l), R2 is a reservoir containing p-nitroaniline (0.002 mole/l) with c. 0.5% sulfuric acid, R3 is a reservoir containing a 1% solution of sulfamic acid in water, C is an aqueous solution, adjusted to pH 4.5, containing 6% of acetic acid, 13.6% of sodium acetate and 4% of sodium chloride, S is a continuous sample stream from the reaction vessel via a by-pass line, P is a pump, L1, L2, L3 and L4 are each a line for mixing the reactant streams, V is an injection valve, and D is a spectrophotometric detector flow cell.

The sample taking system employed is one with continuous filtration, whereby the product, which is present in the reaction mass as a solid, is separated almost completely.

Figure 2:
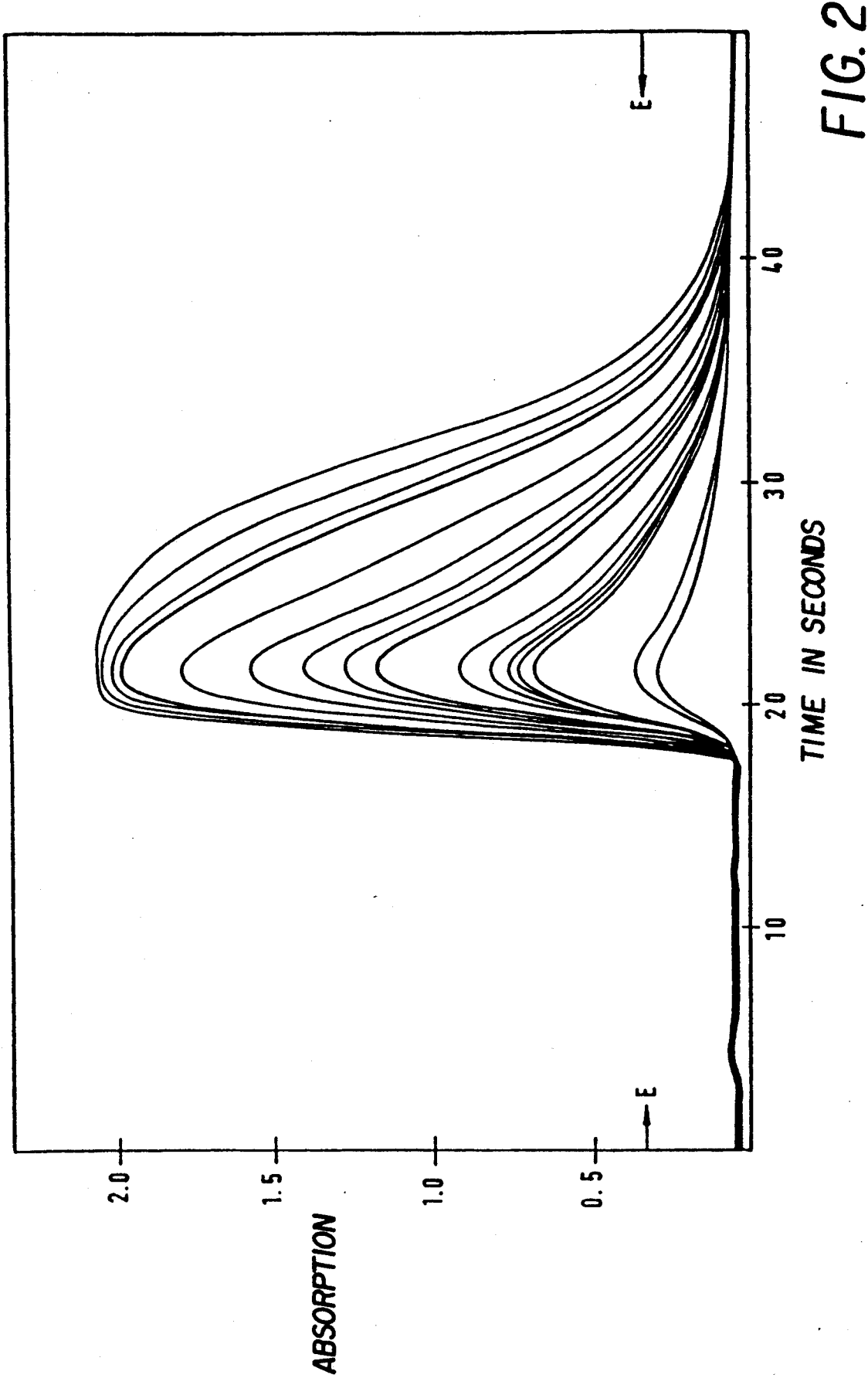
FIG. 2 illustrates the course of an acylation reaction controlled by means of flow injection analysis up to the end point (E), with overlay representation of the sequence of peaks.

In the analyzer, the thermally unstable diazonium ion of p-nitro-aniline is continuously prepared from the amine in the presence of hydrochloric acid and the aqueous solution of sodium nitrite. The addition of sulfamic acid is necessary to destroy excess nitrite. The reaction product of the diazonium ion and the injected sample is recorded spectrophotometrically in the visible absorption of the azo dye formed in the presence of the educt. The selected reagent concentration saturates the analyzer at an absorbance of about 2. Contamination caused by adsorption of dye at the tube walls or optical cell windows is prevented by the carrier solution so as to maintain a stable baseline. The analyzer shows linear response to educt concentrations of up to 700 ppm, beyond which the signal levels off into saturation. FIG. 2 shows the reaction course up to the end point. FIG. 2 shows a sequence of signals recorded after addition of c. 90% of the acylating agent up to the predetermined end point (E). The precision of peak height measurement is sufficient at c. 1% relative standard deviation, and the precision of peak width measurement is acceptable at c. 2% relative standard deviation to assess the starting concentration of educt as well as the concentration of educt after addition of c. 90% of the acylating agent. Process control to the predetermined end point (E) of quality is made after addition of c. 90% of the acylating agent by continuous peak height measurement.

Figure 3:
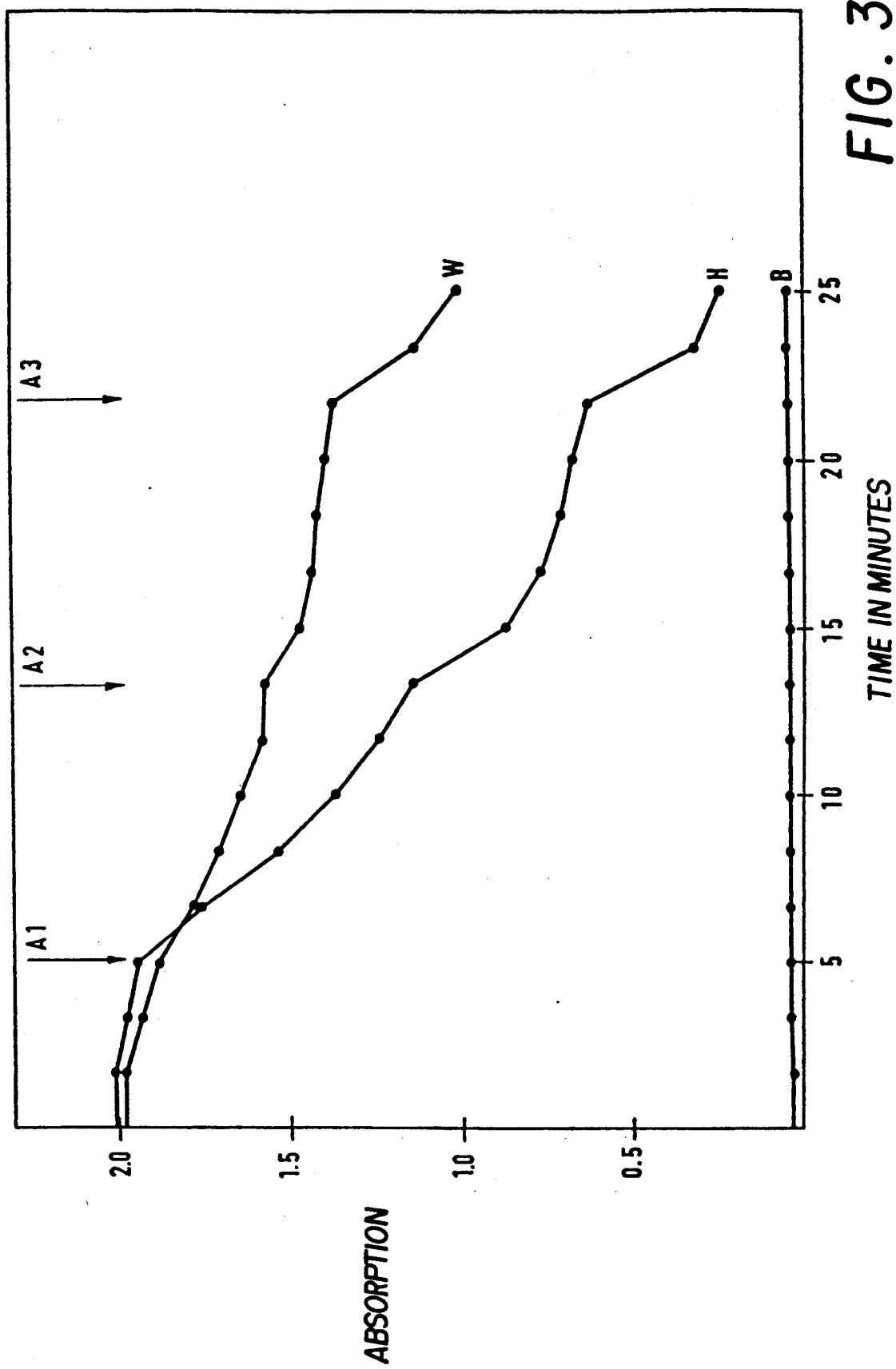
FIG. 3 shows the response of a flow injection analyzer to 3 additions ($A_1$, $A_2$ and $A_3$) of acylating agent to the reaction mass close to the end point of the reaction, with H being the data from peak height measurement and W the data from peak width measurement, and B illustrating the baseline values. To show both methods of evaluation together in one plot the values of a time scale for the peak width measurement (W) were converted to virtual absorbance values.

FIG. 3 shows the values for simultaneous peak height (H) and peak width (W) measurement of the azo dye after addition of acylating agent ($A_1$, $A_2$ and $A_3$) to drive the process to the end point. (B) indicates the stability of the baseline. FIG. 3 is representative of the response of an analyzer to 3 additions of acylating agent to the reaction mass close to the end point of the reaction. For peak width measurement, the values of time axis are converted to virtual absorbance values so as to show both measurements (H) and (W) in the same plot.

The data measured by the detector are evaluated by computer, stored, and used for further process control.

Concentrations of up to 20,000 ppm can be measured with the above evaluation of the data of peak width measurement without changing the flow injection system, i.e. by combining the measuring methods, peak height and peak width measurement, it is possible to cover a large concentration range.

The peak width is approximately proportional to the logarithm of the analyte concentration of the sample. The peak width can be measured at any height above the baseline. Close to the baseline and to the peak maximum, less precise data are obtained than in the range between these extremes, due to interference and a low peak width.

Figure 1:
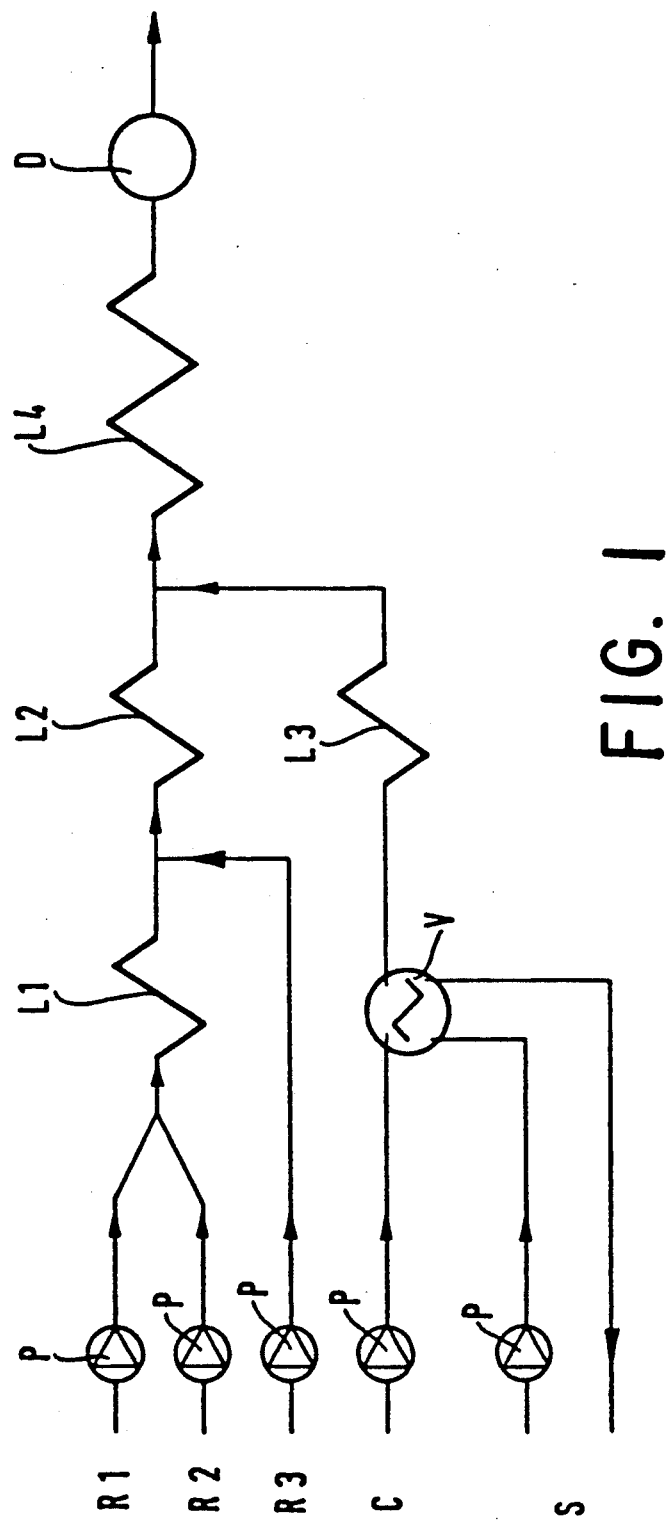
FIG. 1 is a schematic of a flow injection analyzer in which $R_1$, $R_2$, $R_3$ and C are each a reservoir for reagent solutions, S is the sample stream, each P is a pump, $L_1$, $L_2$, $L_3$ and $L_4$ are each a capillary for mixing the reactant streams, V is an injection valve and D is a spectrophotometric detector flow cell.

A somewhat different dispersion profile is obtained by replacing the capillary L4 in FIG. 1 by a mixing chamber as described in Example 2; the mixing chamber and capillary L4 both have the same dead volume. The calibration curve of the peak width measurement thereby becomes steeper and as a consequence the precision improves.

Instead of measuring peak width, it is also possible to apply so-called electronic dilution to extend the dynamic range for measurement. In addition to the determination of the peak maximum, this method makes use of absorbance values at different points on the descending branch of the gradient. Each of these points covers a limited concentration range of the sample with a linear calibration. The precision of this measurement is best at the peak maximum and deteriorates with increasing distance from the peak maximum when measurements are taken on the descending branch of the gradient.

The diazotisation of an amine for driving a process to the end point can be monitored and controlled in a manner corresponding to that described in this Example. In the analyzer 1,3-phenylenediamine-4-sulfonic acid acylated with 2,3-dibromopropionyl chloride in accordance with Example 1, is coupled after diazotisation with sodium nitrite in a solution containing hydrochloric acid, to a coupling component, e.g. N,N-diethylaniline, 3-methyl-N,N-diethylaniline or 1-(3'-chlorophenyl)-3-methylpyrazole. The diazotisation is controlled by determining the nitrogen trioxide concentration. During the diazotisation, which is carried out with sodium nitrite and hydrochloric acid in the presence of an amine, nitrogen trioxide forms via nitrous acid as an intermediate and is reacted with the amine to form the diazonium compound. In the course of the diazotisation the addition of nitrite or amine will conveniently be controlled via the intensity of the recorded signal, i.e. when the signal has reached a rated value defined by preliminary experimentation, the addition of nitrite or amine is corrected accordingly. In this manner it is possible to avoid overaddition of nitrite and also to control the addition of nitrite during the reaction such that no unwanted by-products are formed.

Reproducible quality of the process product, the diazonium salt of 1-amino-3-(2',3'-dibromopropionylamino)benzene-6-sulfonic acid, is ensured by on-line process control. An azo coupling reaction is carried out as the analytical reaction in the analyzer. The analyzer operates as follows:

The reaction mass flows continuously via a by-pass line past a valve which injects samples of the reaction mass into a carrier solution (hydrochloric acid solution) at fixed intervals of time. This carrier solution transports the reaction mass to a gas diffusion cell, e.g. with teflon membrane, so that $N_2O_3$ diffuses through the membrane of the gas diffusion cell into a recipient carrier solution (0.03% of sulfanilic acid in 0.1N hydrochloric acid). The $N_2O_3$ effects partial diazotisation of the sulfanilic acid. A 0.03% aqueous solution of 1-phenyl-3-methylpyrazolone, which is adjusted to pH 10 with borax, is fed into this stream of partially diazotised sulfanilic acid.

The resultant azo dye is recorded in a spectrophotometric detector flow cell at a wavelength of 430 nm. The absorbance changes in accordance with the concentration of $N_2O_3$ present in the carrier solution, i.e. in accordance with the state of the diazotisation in the reaction mass. A sudden rise in the recorded peak height indicates the imminent end of the diazotisation.

The values recorded in the detector are fed into a computer, stored, and used for process control.

EXAMPLE 2

Preparation of Dinitrostilbenedisulfonic Acid to Exemplify Process Control by Flow Injection Analysis Process: Dinitrostilbenedisulfonic acid is prepared from p-nitrotoluenesulfonic acid by oxidation at 90° C. with sodium hypochlorite in strongly alkaline medium. Colourless and coloured by-products are formed in the process. Their concentration is determined by reaction conditions and reaction time, as the product is not stable under the reaction conditions. It is therefore necessary to find the optimum time at which as much educt and intermediate as possible are consumed but as little product as possible is decomposed. The electrochemical potential of the reaction mass must be kept constant during the reaction in order to ensure high yield and good product quality. This is achieved by constant control of the electrochemical potential and correcting deviations by addition of sodium hypochlorite. The electrochemical potential of the reaction mass is measured during the entire reaction with an electrode.

Too small an amount of oxidising agent induces the formation of yellow by-products which absorb at 450 nm, whereas the normal amount of oxidising agent, in particular an excess of oxidising agent, decomposes the product (absorption of the product at 353 nm) to by-products which absorb in a spectral range that overlaps with the range of the educt (maximum at 280 nm).

Figure 4:
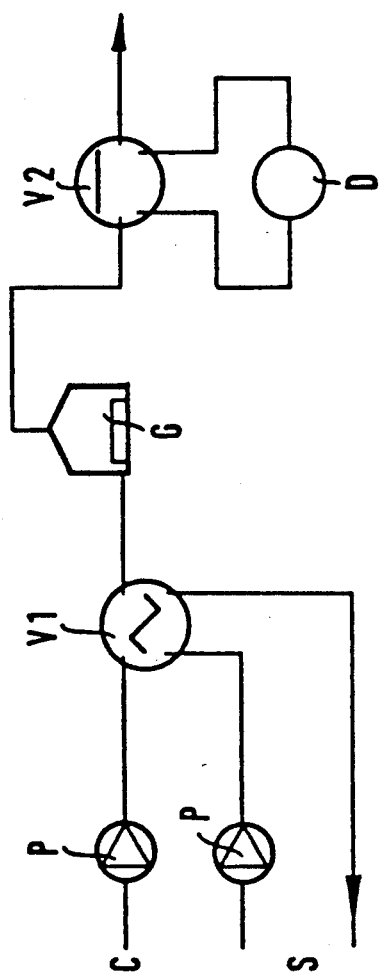
FIG. 4 shows a flow injection analyzer in which C is a carrier stream, S is the sample stream, each P is a pump, $V_1$ and $V_2$ are each injection valves, G is a magnetically stirred mixing chamber, and D is a spectrophotometric detector flow cell.

Flow injection analyzer: corresponds to the assembly shown in FIG. 4, wherein

C is an aqueous carrier stream,
S is the hot sample stream of 90° C. from the sample taking system,
P is a pump,
V1 is an injection valve,
V2 is an injection valve for selecting and trapping a zone of the gradient of the sample zone,
G is a magnetically stirred mixing chamber, and
D is a spectrophotometric detector flow cell.

Figure 5:
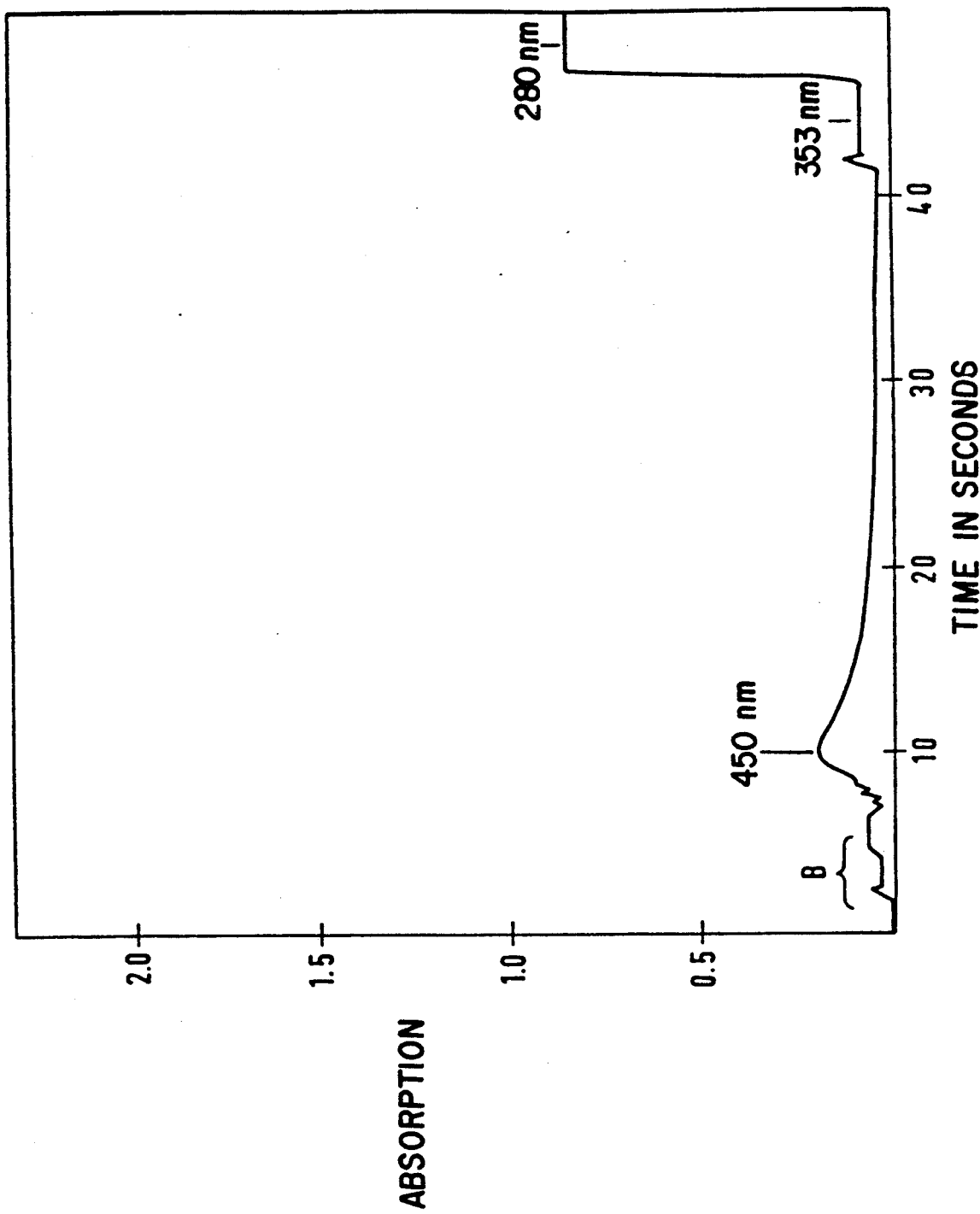
FIG. 5 shows the course of the preparation of dinitrostilbenedisulfonic acid controlled by flow injection analysis at the start of the reaction, B being the baseline absorbance.

The flow injection analyzer illustrated in FIG. 4, which requires high temperatures and a high rate of flow to prevent crystallisation in the sample circuit, consists in principle only of a part for sample processing in conjunction with the detector. By switching on the injection valve (V2 in FIG. 4), small volumes (e.g. 20 µl) of the diluted sample zone can be kept stationary in the flow cell. The mixing chamber with a capacity of 500 µl serves mainly to prevent the product from precipitating and to effect an immediate drop in temperature of the hot sample zone to quench further reaction. Further, the mixing chamber produces a gradient of the injected sample for the baseline corrected spectrophotometric measurement at two different dilutions and in three different spectral ranges. FIG. 5 shows the initial phase of the process. Shortly before the injection of the process sample, the baseline absorption is determined at 280 nm and 353 nm relative to the absorption at 450 nm (B in FIG. 5). The concentration gradient of the sample which exits from the mixing chamber is recorded at 450 nm and the absorbance at peak maximum is determined. The baseline corrected absorbance of the trapped sample zone (V2 in FIG. 5; 20 µl) is measured at 353 and 280 nm at a dilution factor of c. 1500.

Figure 6:
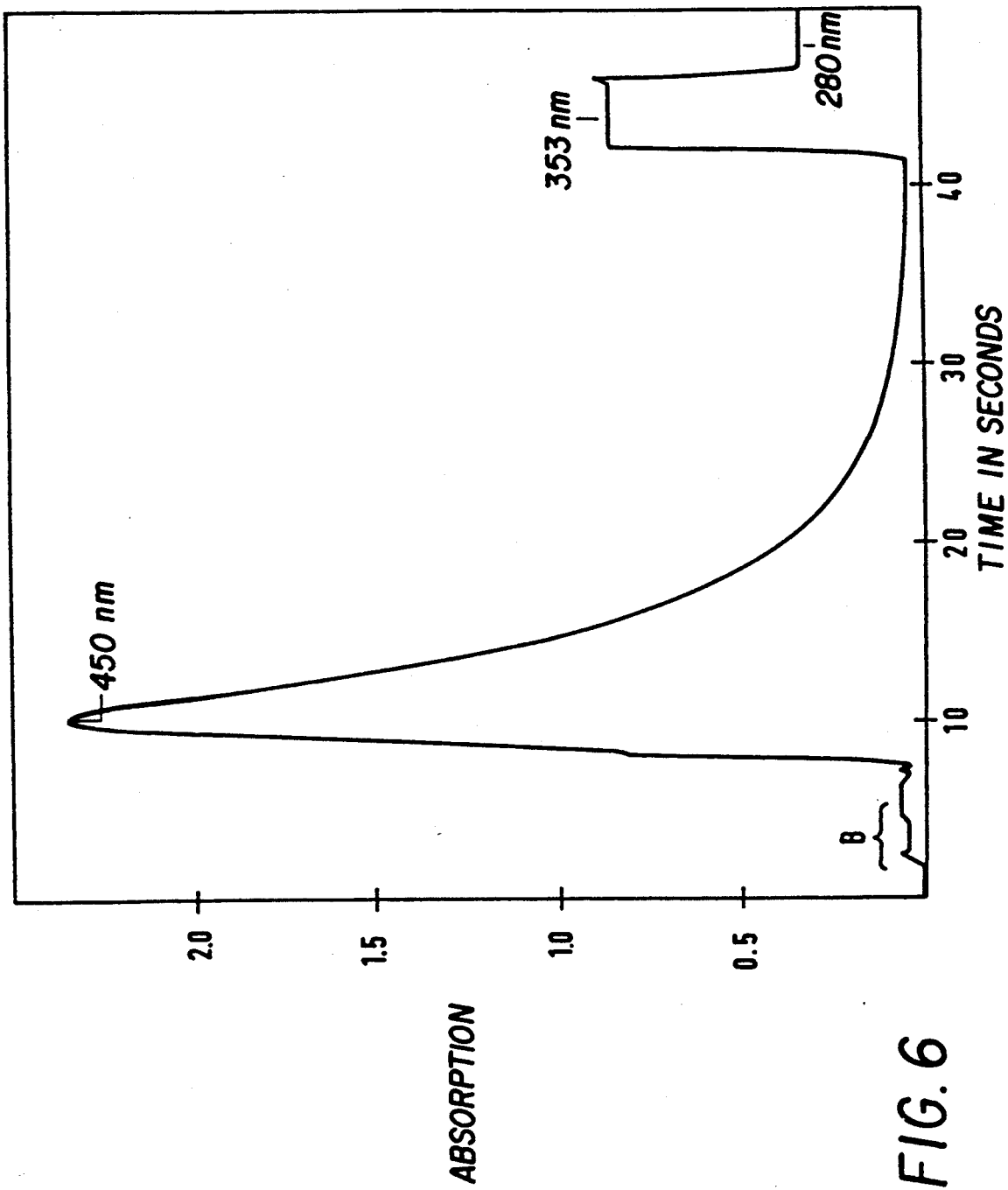
FIG. 6 shows the end phase of the preparation of dinitrostilbenedisulfonic acid controlled by flow injection analysis.

FIG. 6 shows the end phase.

90 individual items of information are obtained per hour at an injection frequency of 30 samples per hour, including sample taking. This amount of data is sufficient for optimum control of the process. The results of the synchronous spectrophotometric control of educt depletion, product formation and the formation of by-products are combined with the results of the less selective electrochemical determination for prognosis (feed-forward control) of the addition of oxidising agent, whereby yield and quality of the product are optimised.

As the analysis at three selected wavelengths with respect to process time and location of sample taking originates from an identical sample, each ratio of the absorbance at different wavelength is independent of the volume of the actual reaction mass. A calibration of the system is superfluous as only relative changes of absorbance values are used as relevant parameters for process control.

Figure 7:
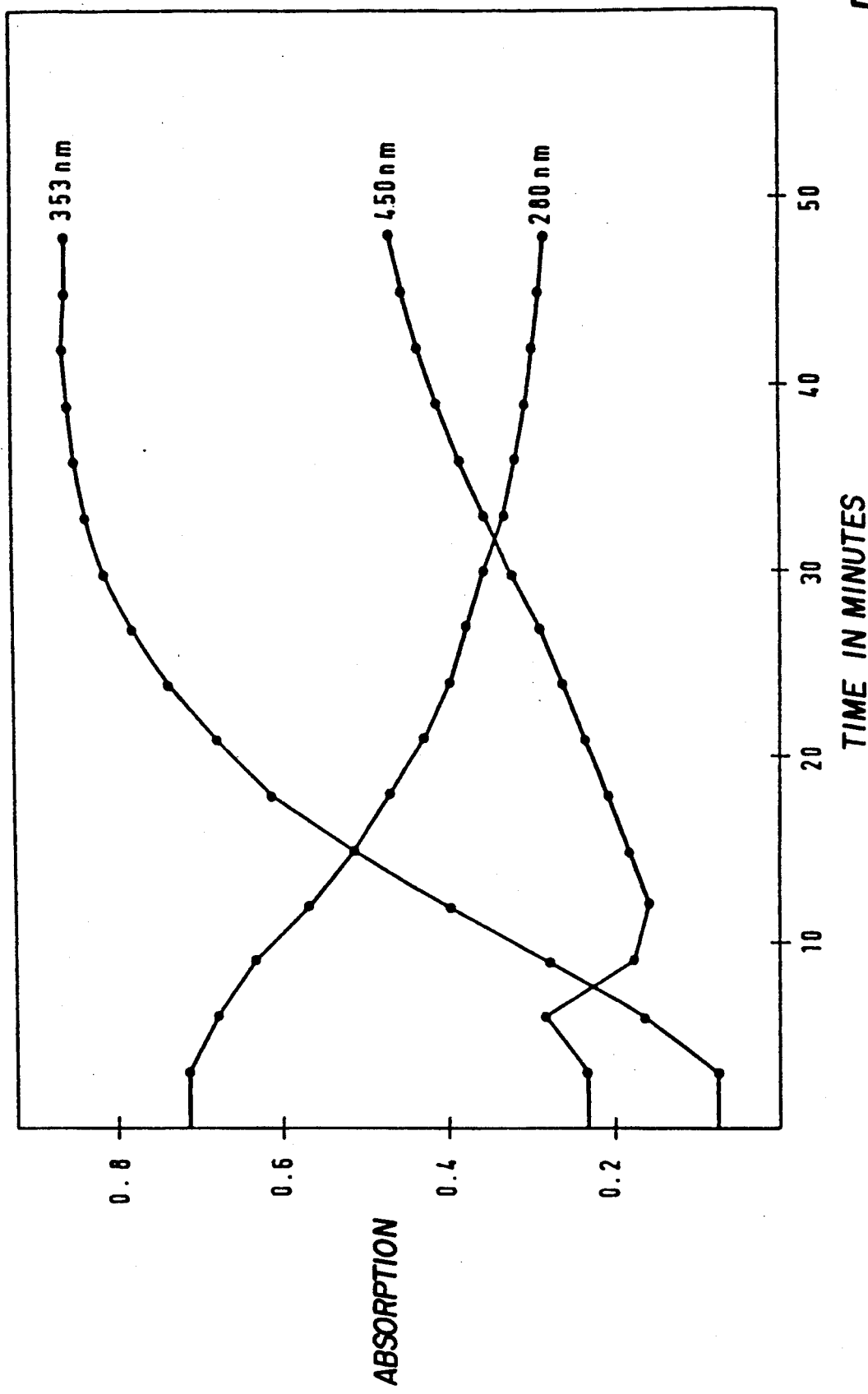
FIG. 7 shows the preparation of dinitrostilbenedisulfonic acid, controlled by flow injection analysis, over the entire reaction course, the absorbance values being corrected for the baseline.

FIG. 7 shows the time-dependent, baseline corrected absorbance values during the entire reaction determined for the above chemical reaction. The values measured at 280 nm show the educt consumption, those measured at 353 nm show product formation, and those measured at 450 nm show the formation of by-products; the latter values were reduced by a factor of 5 for illustration in FIG. 7.

EXAMPLE 3

Process for the Preparation of the Azo Dye from Diazotised P-nitroaniline and H-acid (1-Amino-8-hydroxynaphthalene-3,6-disulfonic Acid) by Means of Control by Flow Injection Analysis [Reversed Flow Injection Analysis]

Process: A reaction kettle is charged with 1-amino-8-hydroxynaphthalene-3,6-disulfonic acid in aqueous solution (pH 10). To this solution is continuously added an aqueous solution of the diazonium salt of p-nitroaniline. After a brief reaction time, an azo dye is obtained which absorbs in the visible range of the spectrum with sufficient spectroscopic selectivity. The reaction solution is pumped constantly at high flow rate from the vessel through the injection valve of the analyzer.

Figure 8:
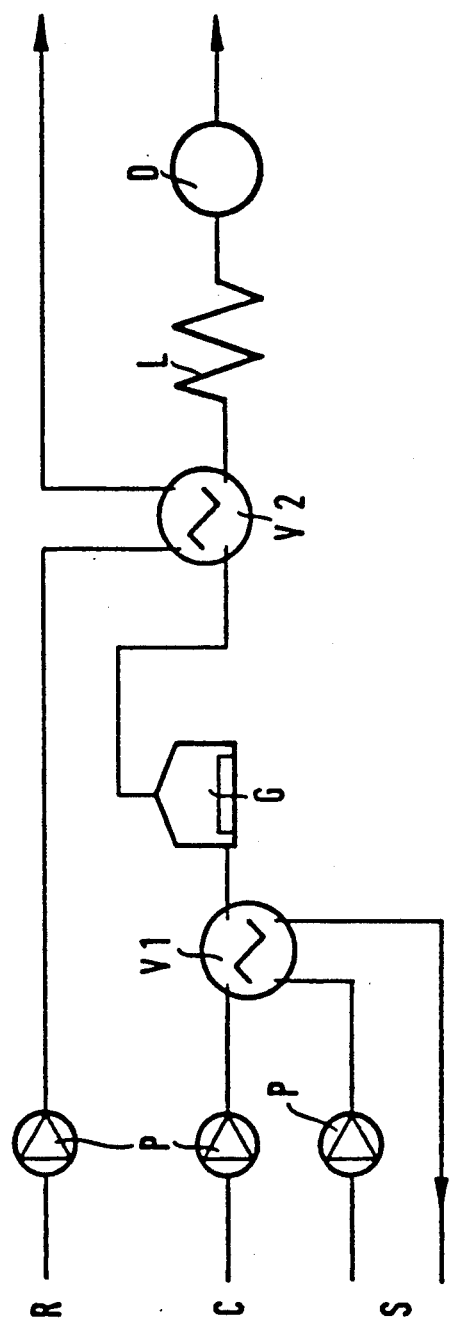
FIG. 8 illustrates an analyzer for measuring in the reversed flow injection mode, where R is a reagent stream, C is a carrier stream, S is the sample stream, each P is a pump, $V_1$ is the valve for injecting the sample, $V_2$ is the valve for injecting the reagents, G is a magnetically stirred mixing chamber, L is a column and D is a spectrophotometric detector flow cell.

Flow injection analyzer: Assembly as shown in FIG. 8, wherein

R is the reagent stream containing c. 0.005 mol/l of the diazonium salt of p-nitroaniline in aqueous solution,
C is an aqueous carrier stream containing a phosphate buffer for adjusting the pH to 8,
S is a sample stream of the sample taking system,
P is a pump,
V1 is a sample injection valve,
V2 is a reagent injection valve,
G is a magnetically stirred mixing chamber,
L is a capillary, and
D is a spectrophotometric detector flow cell.

Figure 9:
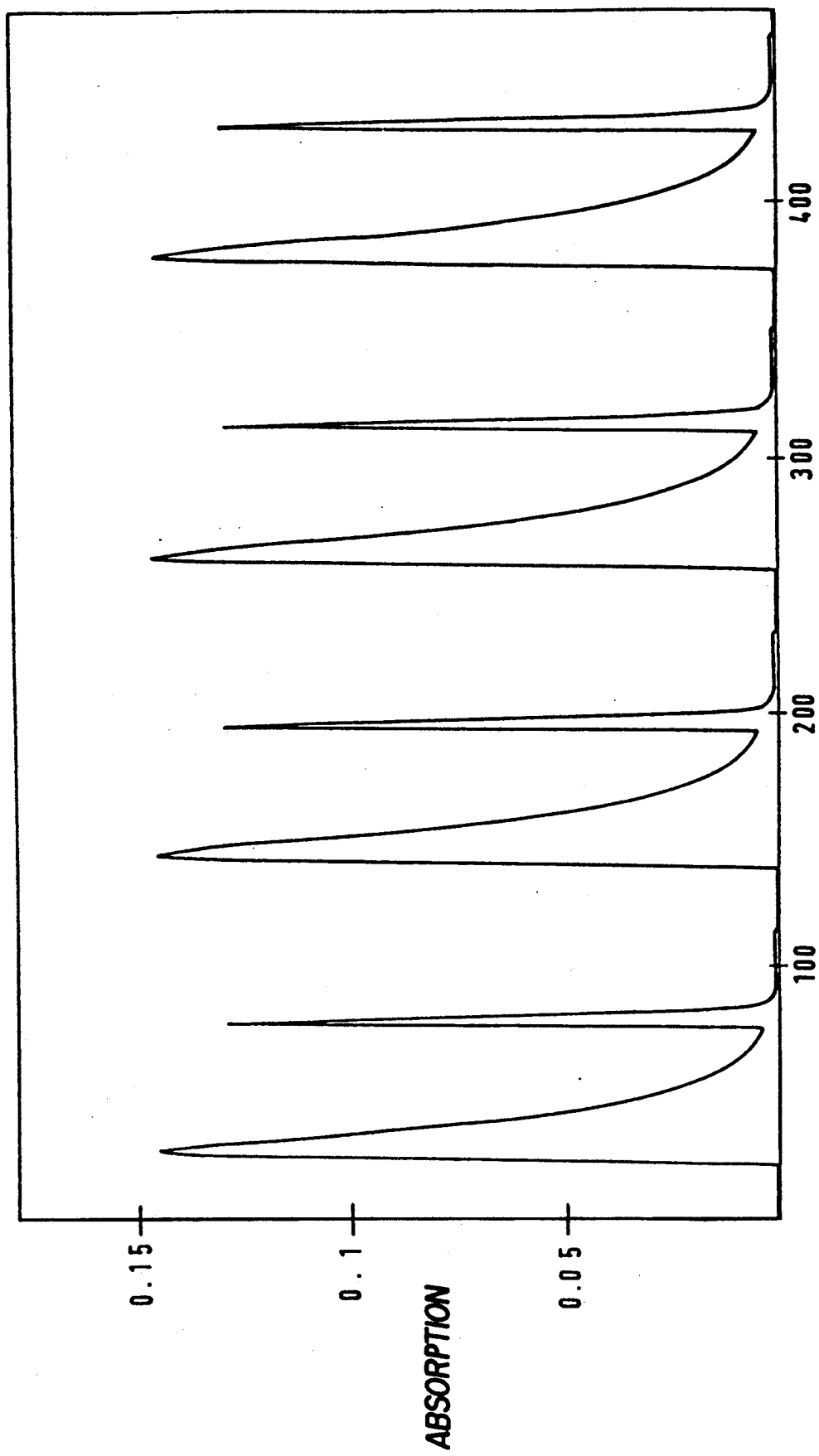
FIG. 9 shows the reproduction of 4 reversed flow injection into gradients of the sample at a dilution coefficient of c. 3000.
Figure 10:
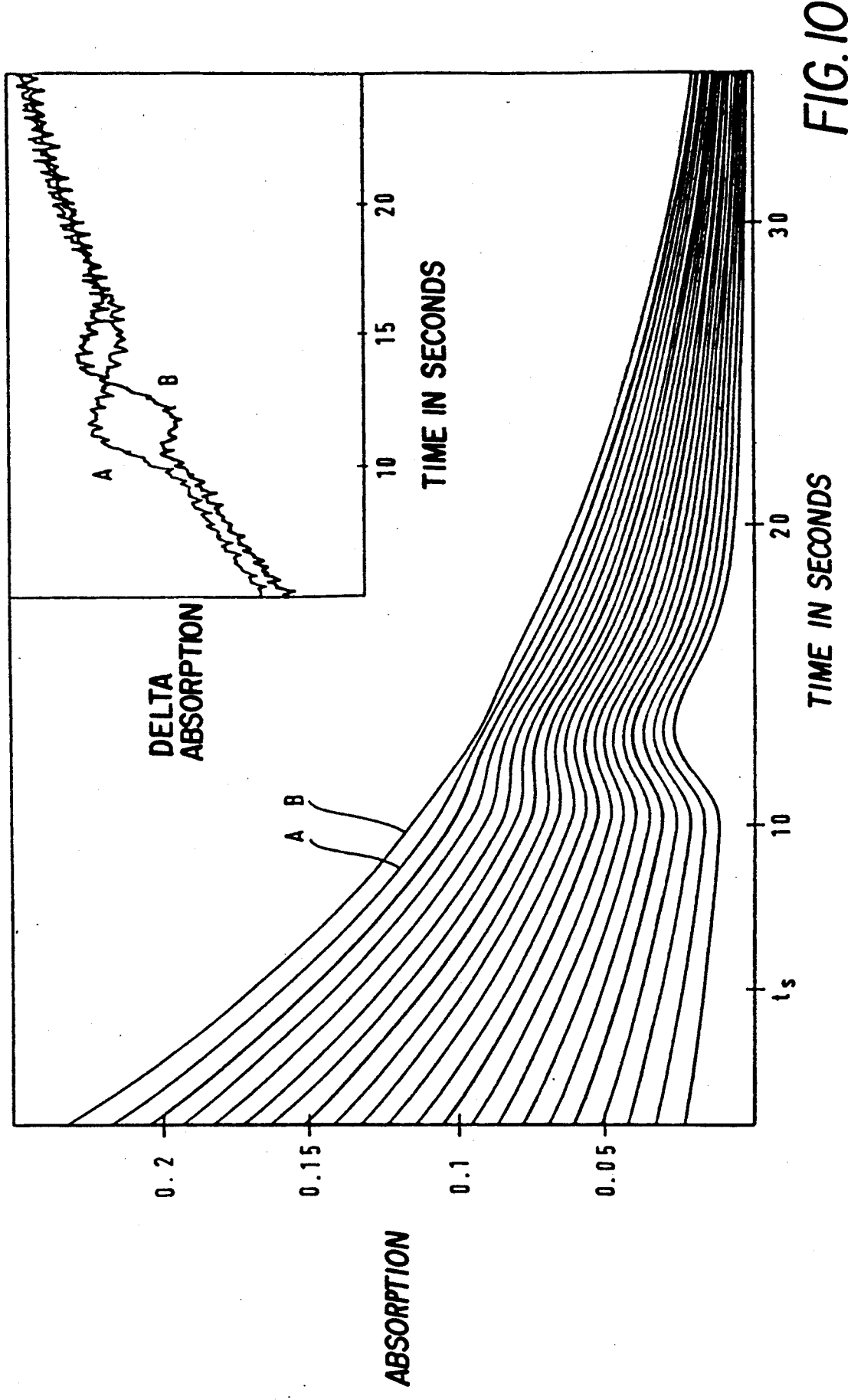
FIG. 10 shows how in the reversed flow injection analysis mode the disappearance of the induced transient into the background signal caused by the formation of an azo dye, with A and B representing the change of phase.

A sample from the reaction vessel is injected continuously into the analyzer at intervals of 150 seconds and immediately mixed with the buffer solution in the mixing chamber. The diluted and pretreated sample zone flows from the mixing chamber through the valve V2. A solution of the same diazonium salt as in the reaction vessel is injected into the gradient of this solution at a dispersion coefficient of c. 3000. The height of the resultant transient, which is recorded on the descending tail of the coloured sample gradient, depends on the concentration of the coupling component in the reaction vessel at the time of sample taking. To obtain a sufficient sensitivity under the conditions of reversed flow injection analysis, the analyzer is optimised in that range of the concentration of the coupling component close to the end point of the reaction. During the process, the background absorption increases proportionately to the formation of the azo dye. FIG. 9 shows the reproduction of 4 reversed flow injections into the gradient of the sample at a dispersions coefficient of c. 3000. Repeatability is ensured. The analyzer provides the following information relevant to process control:

1. The background absorbance of the diluted gradient, measured at an arbitrarily selected time $t_s$, is directly related to the concentration of the azo dye formed in the course of the process. A high frequency of analysis with regard to the overall process time makes possible a prognosis on the end point of the process after each single analysis.
2. A prognosis on the end point of the process can be made from each individual injected sample via the consumption of coupling component, which results from the peak height of the transient induced in the analyzer.
3. The disappearance of the induced transient into the background signal of the azo dye occurs at a specific point in time of the process, q.v. A and B in FIG. 10. This point is detectable as change of phase of the first derivative of the transient signal, q.v. insert in FIG. 10. The process time at which this change of phase occurs corresponds to a well defined residual concentration of unreacted coupling component. This residual concentration must be determined by some other analytical means (e.g. chromatography). Provided the process is run reproducibly from batch to batch under physical and chemical control, the time of the change of phase constitutes a defined process state with respect to product formation and educt consumption, thus making possible optimum process control.

The mode of process control described in this Example is generally applicable to processes which suffer from strong background interference, e.g. the absorption of an azo dye formed in the course of the process.

In FIGS. 2, 3, 5, 6, 7, 9, 10 and 11, absorption means absorbance or extinction.

What is claimed is:

1. A method on on-line controlling and optimizing processes for the manufacture of textile finishing and improving agents and their intermediates which comprises the steps of
   (a) automatically sampling, over at least a last portion of the processes,
   (b) injecting samples from step (a) into a carrier stream, and then
   (c) transporting the carrier stream to a spectrophotometric detector,
   (d) spectrophotometrically measuring at least one characteristic of the samples,
   (e) controlling the process to an optimum end point based on at least one of said characteristics, and
   (f) repeating steps (a) through (e).

2. The method of claim 1 wherein the samples from step (a) are physically or chemically manipulated between steps (b) and (c).

3. The method according to claim 1 wherein said processes are discontinuous.

4. The method according to claim 1 wherein said finishing and improving agents are dyes, fluorescent whitening agents and their intermediates.

5. The method according to claim 1 wherein said processes are single-phase or multi-phase preparatory processes.

6. The method according to claim 1 wherein the characteristic which is measured in step (d) is a simultaneous peak height and peak width recorded by the spectrophotometric detector.

7. The method according to claim 1 wherein the characteristic which is measured in step (d) is absorbence values detected by the spectrophotometric detector at different fixed points in time after detection of a maximum value.

8. The method according to claim 1 wherein said processes are acylation reactions.

9. The method according to claim 1 wherein said processes are diazotization reactions.

10. The method according to claim 9 wherein said processes are diazotization reactions wherein a sample is taken through a gas diffusion membrane.

11. The method according to claim 1 wherein said processes are coupling reactions.

12. The method according to claim 1 wherein the samples from step (a) are pretreated by means of continuous filtration, homogenization or dilution with a solvent or with a membrane before injecting said samples into the carrier stream of step (b).

* * * * *